US012629229B2

(12) United States Patent
Marsh et al.

(10) Patent No.: US 12,629,229 B2
(45) Date of Patent: May 19, 2026

(54) LIGHT CARRIER AND ILLUMINATION SYSTEM FOR A SURGICAL TUBE

(71) Applicant: Sunoptic Technologies, LLC, Jacksonville, FL (US)

(72) Inventors: Kim A. Marsh, Naples, FL (US); Walter Antonio Orozco, Jacksonville, FL (US)

(73) Assignee: Sunoptic Technologies, LLC, Jacksonville, FL (US)

( * ) Notice: Subject to any disclaimer, the term of this patent is extended or adjusted under 35 U.S.C. 154(b) by 318 days.

(21) Appl. No.: 18/129,452

(22) Filed: Mar. 31, 2023

(65) Prior Publication Data

US 2023/0270520 A1    Aug. 31, 2023

Related U.S. Application Data

(63) Continuation-in-part of application No. 16/711,784, filed on Dec. 12, 2019, now abandoned.

(Continued)

(51) Int. Cl.
*A61B 90/30* (2016.01)
*A61B 1/00* (2006.01)
(Continued)

(52) U.S. Cl.
CPC .......... *A61B 90/30* (2016.02); *A61B 1/00163* (2013.01); *A61B 1/00165* (2013.01); *A61B 1/00167* (2013.01); *A61B 1/0017* (2013.01); *A61B 1/06* (2013.01); *A61B 1/0607* (2013.01); *A61B 1/0615* (2013.01); *A61B 1/0623* (2013.01); *A61B 1/0625* (2022.02); *A61B 1/0669* (2013.01); *A61B 1/07* (2013.01); *A61B 1/32* (2013.01); *A61B 2017/00734* (2013.01);

*A61B 2017/00946* (2013.01); *A61B 17/0218* (2013.01); *A61B 17/025* (2013.01);
(Continued)

(58) Field of Classification Search
CPC . A61B 17/3421; A61B 17/34; A61B 17/3415; A61B 17/3423; A61B 17/3468; A61B 17/02; A61B 17/0218; A61B 17/025; A61B 2017/345; A61B 2017/3445; A61B 2017/00946; A61B 90/30; A61B 1/00165; A61B 1/07; A61B 1/06; A61B 1/0607; A61B 1/32; A61B 1/0625; A61B 1/0669; A61B 1/0017; A61B 1/0615; A61B 1/0623; A61B 1/0661; A61B 1/0676; A61B 1/00163; A61B 1/00167; A61B 2090/00734; A61B 2090/309; A61B 2090/306; A61B 2017/00734; F21V 21/0885; F21L 4/04
USPC .................................................... 600/200–249
See application file for complete search history.

(56) References Cited

U.S. PATENT DOCUMENTS

| | | | | |
|---|---|---|---|---|
| 6,228,025 B1 * | 5/2001 | Hipps | .............. | A61B 17/00008 600/245 |
| 2005/0165283 A1 * | 7/2005 | Hestad | ................... | A61B 17/02 600/212 |
| 2016/0361133 A1 * | 12/2016 | Davis | ................. | A61B 17/3211 |

\* cited by examiner

*Primary Examiner* — Marcela I. Shirsat
(74) *Attorney, Agent, or Firm* — William E. Noonan

(57) ABSTRACT

A light carrier for engaging a surgical tube includes unitarily and communicably interconnected inlet, intermediate and channel sections composed of a light conducting material. The channel section is laterally concave and has a light projecting surface portion. The channel section is introduced into the surgical tube and light introduced through the inlet section is transmitted through the light carrier and projected into the tube to illuminate a medical or surgical procedure being performed through the tube.

16 Claims, 8 Drawing Sheets

Related U.S. Application Data

(60) Provisional application No. 62/778,564, filed on Dec. 12, 2018.

(51) Int. Cl.

| | |
|---|---|
| *A61B 1/06* | (2006.01) |
| *A61B 1/07* | (2006.01) |
| *A61B 1/32* | (2006.01) |
| *A61B 17/00* | (2006.01) |
| *A61B 17/02* | (2006.01) |
| *A61B 17/34* | (2006.01) |
| *F21L 4/04* | (2006.01) |
| *F21V 21/088* | (2006.01) |

(52) U.S. Cl.
CPC ....... *A61B 17/3415* (2013.01); *A61B 17/3421* (2013.01); *A61B 17/3423* (2013.01); *A61B 2017/3445* (2013.01); *A61B 2017/345* (2013.01); *A61B 17/3468* (2013.01); *A61B 2090/306* (2016.02); *A61B 2090/309* (2016.02); *F21L 4/04* (2013.01); *F21V 21/0885* (2013.01)

FIBEROPTIC LIGHT SOURCE

42

10

18

22

20

12

42

18

22

10

20

LIGHT CARRIER AND ILLUMINATION SYSTEM FOR A SURGICAL TUBE

RELATED APPLICATION

This application is a continuation in part of U.S. application Ser. No. 16/711,784 filed Dec. 12, 2019, which claims the benefit of U.S. Provisional Application No. 62/778,564 filed Dec. 12, 2018.

FIELD OF THE INVENTION

This invention relates to a surgical illumination system featuring alight carrier or guide that securely and effectively engages a surgical cannula or tube of the type used for spinal surgery and other surgical and medical procedures.

BACKGROUND OF THE INVENTION

Surgeons and other medical personnel commonly employ a tubular surgical instrument, such as a cannula, during spinal surgery and various other types of surgical/medical procedures. Such surgical tubes are especially effective for use during minimally invasive spinal surgery and permit the surgeon to introduce surgical instruments into the patient's body so that surgery may be effectively performed on the spine or other part of the body being treated.

Providing adequate lighting for minimally invasive spinal and other types of orthopedic surgery can be problematic. It can be particularly difficult to provide adequate illumination when working through a narrow surgical tube. Improving illumination would facilitate such surgery and contribute to improved surgical outcomes.

SUMMARY OF THE INVENTION

It is therefore an object of the present invention to provide a light carrier that more effectively illuminates surgical and medical procedures performed through a surgical tube so that significantly improved surgical outcomes are achieved.

It is a further object of this invention to provide a light carrier that is adapted to be quickly, reliably and securely fit into surgical tubes having an assortment of diameters and lengths for effectively Illuminating different surgical applications.

It is a further object of this invention to provide a light carrier for a surgical tube that features a relatively simple one piece construction and which is easy to install and utilize for various surgical and medical purposes.

It is a further object of this invention to provide a surgical or medical light carrier that can be quickly, securely and effectively mounted to various types of tubular surgical and medical instruments for illuminating respective surgical and medical procedures as required.

It is a further object of this invention to provide for a light carrier that is especially effective for improving lighting of minimally invasive surgical procedures involving the use of a surgical cannula or other tubular surgical instrument.

This invention relates to a light carrier for engaging a surgical tube to illuminate a surgical site and a surgical procedure being performed through the surgical tube. The light carrier includes a light inlet section composed of a light conducting material for communicably interconnecting with a source of light. The light carrier also includes an intermediate section unitarily and communicably connected to the inlet section and also composed of the light conducting material for transmitting light from the inlet section therethrough. A laterally concave distal channel section is unitarily and communicably interconnected to the intermediate section. The channel section is likewise composed of the light conducting material and includes a light projecting outer surface portion. The channel portion is insertable into the surgical tube such that light conducted through the channel section is projected from the carrier through the surgical tube to illuminate the surgical site and the procedure being performed.

In a preferred embodiment, the channel section is composed of a resiliently flexible material such that the channel section is laterally compressible for inserting into a surgical tube having a diameter that is smaller than the uncompressed lateral width of the channel section. The resiliently flexible composition of the channel section may allow the channel section to laterally conform to an interior surface of the surgical tube into which the light carrier is inserted. The intermediate section may be longitudinally flat or curved. The channel section may be unitarily interconnected to the intermediate section by a light conducting transition section that is configured such that the lateral width of the channel section is greater than the lateral width of the intermediate section. An opaque portion of the intermediate transition and channel sections of the carrier may be covered by an overmold to restrict projection of light from the light carrier through the opaque portion.

This invention also features an illuminated surgical tube assembly. The assembly employs a cannula or other type of surgical or medical tube. The light carrier, as previously described, is inserted into the tube and operably connected to a light source. This causes light to project through the tube and illuminate the procedure.

The light carrier may be operably interconnected to the light source by a fiberoptic interface. The interface may include a tubular coupler having a flat slot that receives the inlet section of the light carrier. The interface may also include an opening for receiving a discharge end of a fiberoptic cable communicably connected to the light source. The cable may carry an annular spring that interengages an interior circumferential groove in the coupler to secure the light carrier to the cable with the inlet section abutting the discharge outlet of the cable.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
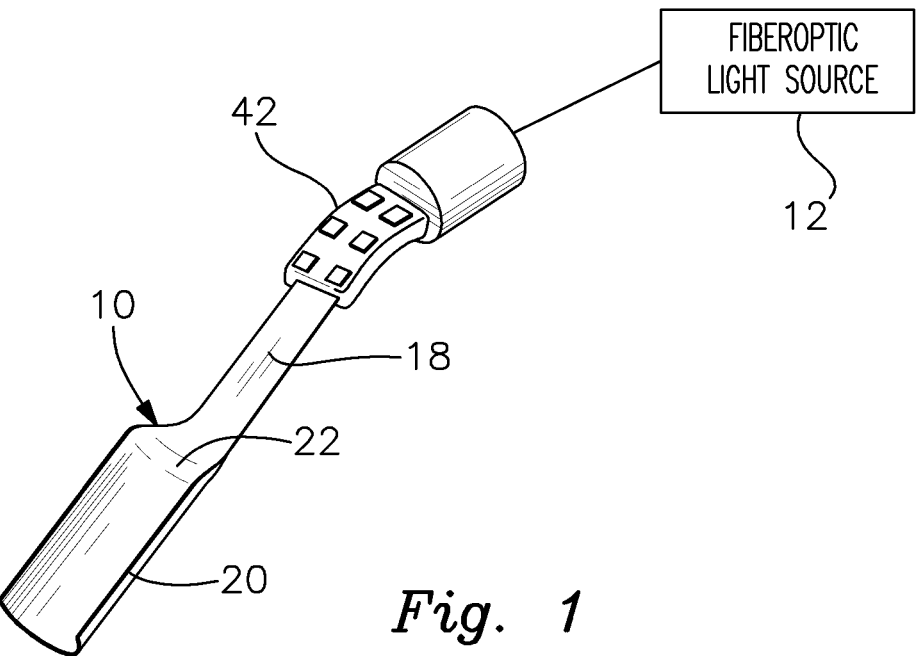
FIG. 1 is a perspective view of a light carrier designed for use with a cannula or other type of surgical tube in accordance with this invention; the light carrier is shown operably attached to a fiberoptic light source.
Figure 2:
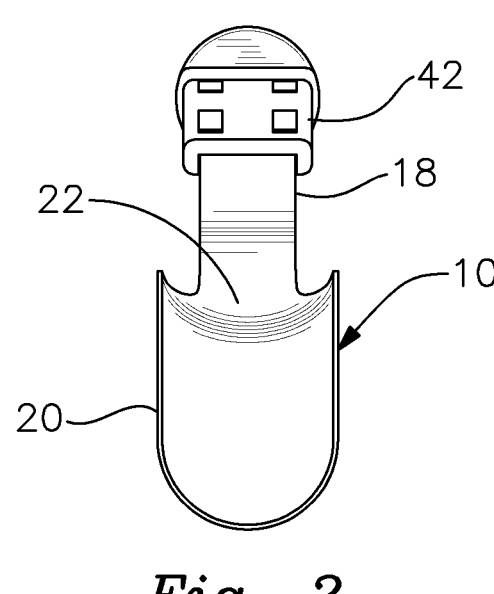
FIG. 2 is a top view of the light carrier shown in FIG. 1.
Figure 3:
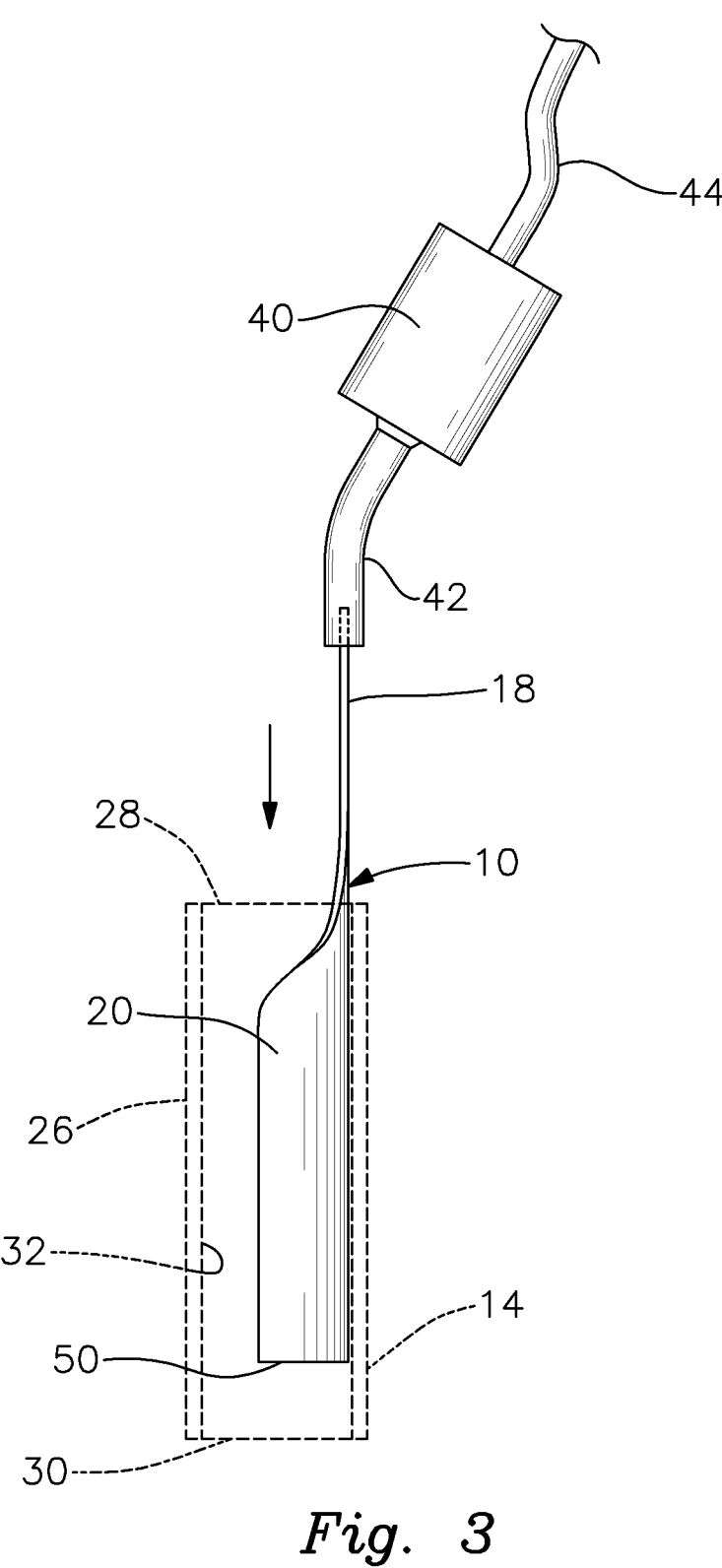
FIG. 3 is an elevational side view of the light carrier attached to a fiberoptic interface and inserted into a surgical tube.

There is shown in FIGS. 1-3 a single-piece light carrier or light guide 10 that is connected to a fiberoptic light source 12, shown schematically in FIG. 1, for illuminating a medical or a surgical procedure performed through a surgical tube 14, shown in phantom in FIG. 3. The surgical tube itself is conventionally employed in various types of medical and surgical procedures. It should be understood that tubular instruments of varying lengths, diameters, curvatures and configurations are commonly utilized during spinal surgery, as well as other minimally invasive operations and medical procedures. Light carrier 10 may be employed with assorted types of surgical tubes and cannulas employed with various medical and surgical devices and procedures. The specific type of tube or cannula with which the carrier may be used is not a limitation of this invention.

Figure 4:
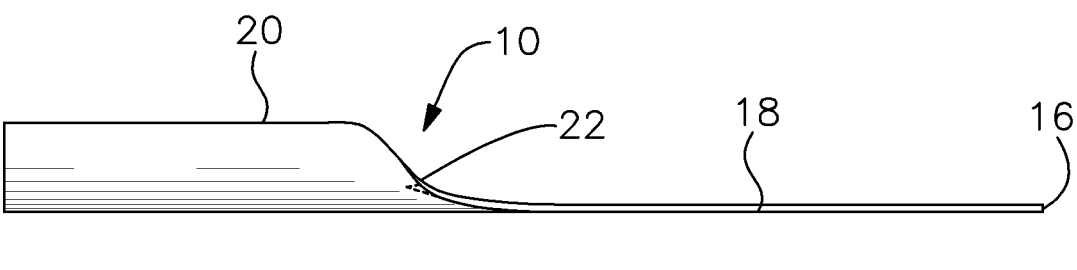
FIG. 4 is an elevational side view of the light carrier.
Figure 5:
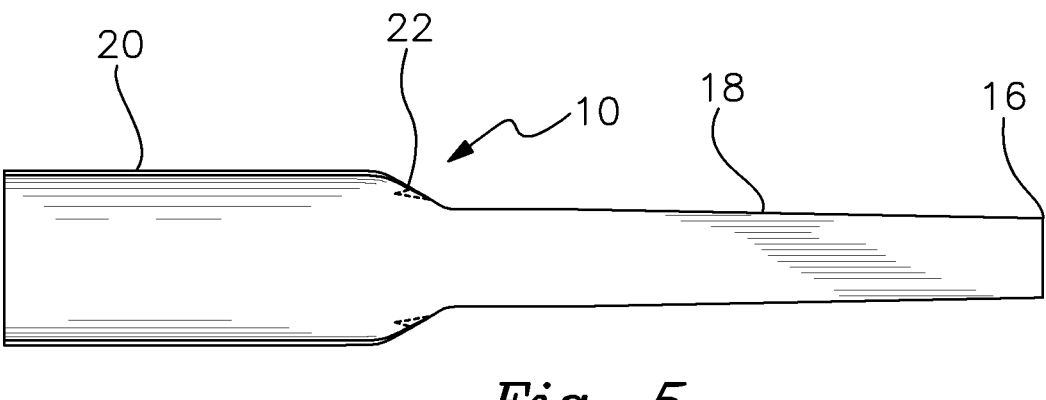
FIG. 5 is a plan view of the light carrier.
Figure 6:
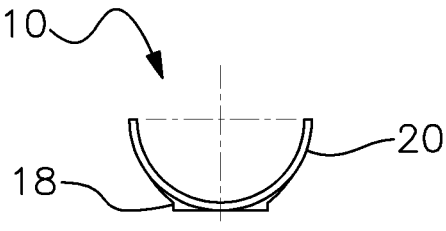
FIG. 6 is an elevational lefthand end view of the light carrier.

Light carrier 10, which is shown alone in FIGS. 4, 5 and 6, comprises a single elongate piece composed of a unitary light conducting material such as clear Makrolon® or an alternative polycarbonate or other material conventionally utilized for light guides and light carriers used in medical and surgical applications. Preferably, the light carrier is resiliently flexible as is described more fully below. As best shown in FIGS. 3 and 4, light carrier 10 includes a light inlet 16 at one end of the carrier. An elongate and substantially flat intermediate section 18 is unitarily and communicably joined to inlet section 16 and extends forwardly therefrom. A laterally concave channel section 20 is formed at the opposite distal end of light carrier 10. Channel 20 is unitarily and communicably interconnected to intermediate section 18 through a transition section 22. Transition section 22 is configured to taper upwardly and laterally outwardly from intermediate section 18 such that channel section 20 is laterally wider than intermediate section 18 (FIGS. 1, 2, 5 and 6). In alternative embodiments, the channel section 20 of the flexible carrier may maintain a flat and nonconcave condition prior to engagement with the surgical tube 20. Again, the light carrier features a unitary, single piece construction and is composed exclusively of a light conducting material.

Although light carrier 10 is preferably composed of a flexible plastic, in alternative embodiments, a more rigid light conducting material may be utilized. The thickness of the light carrier as well as its overall dimensions, both longitudinally and laterally, may be varied within the scope of this invention. Because the device is often intended for use in diametrically small tubes, in certain cases the thickness of the carrier can be approximately 0.03 inches.

Channel section 20 includes a light projecting portion, which typically comprises the outer surface of the channel section. Indeed, virtually the entire outer surface of the light carrier, including the intermediate section and transition section is also able to project light unless the carrier is modified by applying an opaque overmold, as is described more fully below.

Figure 7:
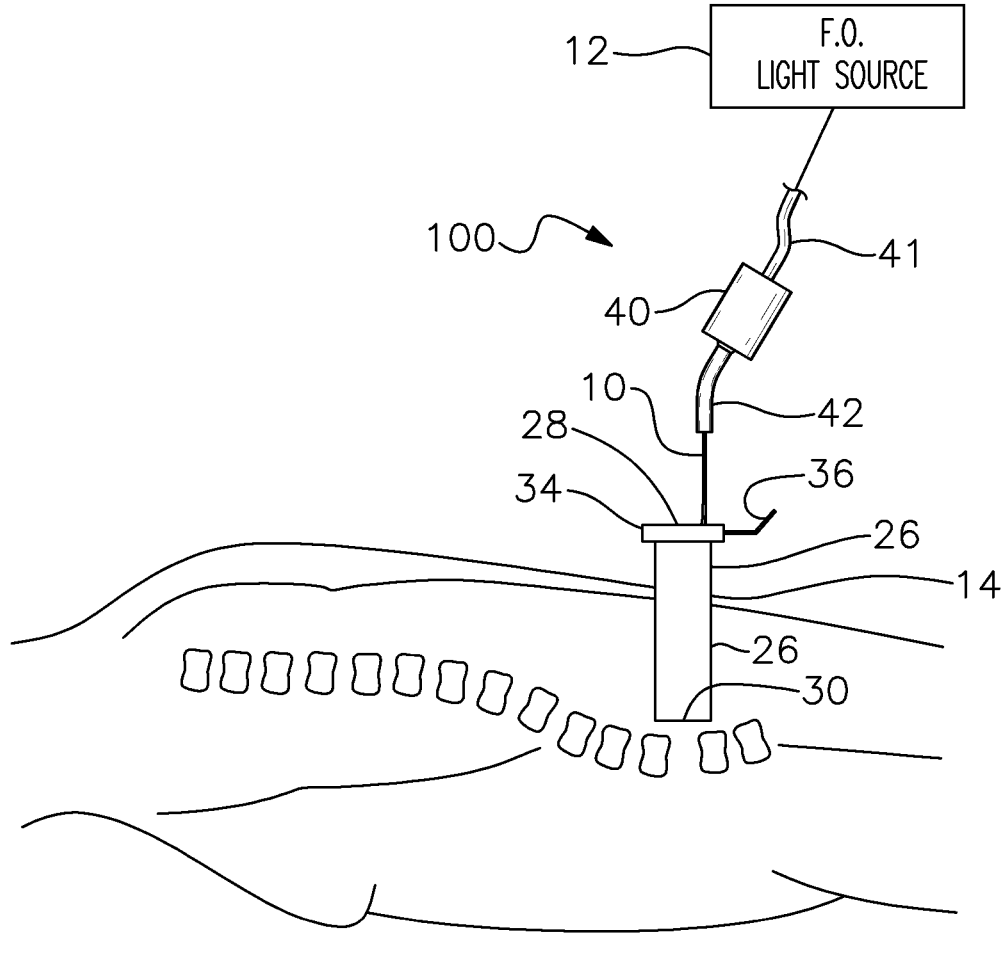
FIG. 7 is a simplified elevational and partly schematic side view showing the illuminated surgical cannula interengaged with a patient's spine during spinal surgery.

Surgical tube 14, FIGS. 3 and 7, includes an elongate tubular body 26 having open upper and lower ends 28 and 30, respectively, and an interior passageway 32 interconnecting open ends 28 and 30. As shown in FIG. 7, an annular lip 34 may surround open upper end 28 and a support arm 36 may be attached integrally to lip 34. This arm allows the tube to be securely mounted to a surgical table or other supportive structure in the operating room, in a manner that will be known to persons skilled in the art.

As shown in FIGS. 1, 3 and 7, light carrier 10 may be interconnected to fiberoptic light source 12 through a fiberoptic interface 40. More particularly, interface 40 includes a tubular flat to round carrier connector 42 that may be angled, as shown in the drawings, or straight. Tubular connector 42 includes a slot or port for receiving the inlet section 16 of light carrier 10 in a manner that communicably connects the light carrier to fiberoptic light source 12. More particularly, light source 12 delivers light through a fiberoptic cable 44 to interface 40 which, in turn, processes and communicably transmits the light signals to the light carrier through connector 42. A particularly preferred interface and connector are described below in connection with FIGS. 12 and 13.

Light carrier 10 and surgical tube 20 are operably interengaged in the manner best shown in FIG. 3. After the light carrier is attached to fiberoptic connector 42, the distal end 50 of channel section 20 is aligned with the open upper end 28 of tube 14. Typically, a light carrier is selected having a lateral width (i.e., the distance between the upper edges of section 20) that is greater than the diameter of interior passageway 32 of tube 14. The light carrier is introduced into interior passageway 32 by squeezing or compressing the edges of channel section 20 together and inserting the compressed channel section into the interior passageway of the surgical tube. It should be understood that in such versions the spring biased channel section is constructed such that it has a normal relaxed or unbiased diameter that is slightly greater than the diameter of the tube's interior passageway. Channel section 20 is compressed and light carrier 10 is inserted into tube 14 until a selected position is achieved in the tube to obtain a desired lighting effect. When the light carrier is positioned within the tube in this manner, the normal spring bias of the material comprising channel section 20 urges the channel section diametrically outwardly against the interior circumferential passageway wall of tube 14. The channel section substantially conforms to the interior wall of tubular passageway 32 and, as a result, light carrier 10 snugly engages and is held within tube 14. The foregoing operation may be performed prior to or after communicably attaching the inlet section 16 of the light carrier to the fiberoptic light source 12.

Upon insertion of the light carrier into the surgical tube, the fiberoptic light source 12 is operated such that light is transmitted through light carrier 10 and projected from the carrier into tube 14. As a result, significantly improved illumination is provided through tube 14 to a surgical site beyond the open lower end 30 of the tube.

FIG. 7 depicts a surgical operation and namely a minimally invasive spinal procedure, performed using a surgical tube 14. Light carrier 10 is again a part of an overall surgical illumination system 100. The light carrier is operably connected through a connector 42, fiberoptic interface 40, and cable 41 to a fiberoptic light source 12. Surgical tube 14 is introduced surgically into the patient's back such that the lower end of the tube engages the patient's spine. As will be understood to persons skilled in the art, surgery on the spine is typically performed using surgical instruments inserted through the interior passageway of tube 14. The tube itself is held by a conventional holder or frame (not shown) that is, in turn, attached to the support arm 36 of tube 14. Light carrier 10 of surgical illumination system 100 is introduced into the tube in the manner previously described and shown in FIG. 3. The compressed or contracted channel section 20 of the light carrier resiliently expands to securely engage and grip the interior walls of the tubular passageway. The distal channel section of the light carrier and, if desired, the transition and intermediate sections extend into the central passageway 32 as represented in FIG. 3, such that the patient's spine and the areas to be surgically operated upon are clearly illuminated. The flexible, spring-biased construction of the light carrier itself holds the light carrier securely in place to achieve consistent and much improved illumination of the area being surgically addressed.

It should be understood that in alternative embodiments the light carrier may be composed of relatively rigid light conducting and projecting materials that do not exhibit the preferred flexibility previously described. In such cases, the light carrier may be configured similarly to the version described above. Such embodiments may be employed in applications where the lateral curvature of the concave channel section matches or closely corresponds to the curvature of the tube being illuminated.

In still other embodiments, it should be understood that the channel section may include a substantially flat configuration throughout the intermediate, transition and channel sections. Prior to being inserted into the surgical tube, the channel section may be essentially flat (similar to the intermediate section) but exhibits sufficient flexibility for it to be folded laterally and inserted into the tubular passageway in the manner previously described. When so inserted, the spring bias of the light carrier urges the channel section to laterally expand within the tube and grip the interior passageway wall of the surgical tube. As a result, the light carrier is secured in place within the tube in a manner analogous to that previously described. Improved illumination of the tube and the surgical site is thereby achieved.

The present invention allows the light carrier to be inserted quickly, conveniently and effectively within various sizes and types of surgical tubes. It is easy to position and adjust the light carrier within the tube to provide a desired illumination effect. Moreover, the thin flexible nature of the tube allows minimally invasive and other types of surgical procedures to be performed effectively and without undue interference from the illumination device. When the surgery is completed, the light carrier may be removed quickly and conveniently from the surgical tube.

Figure 8:
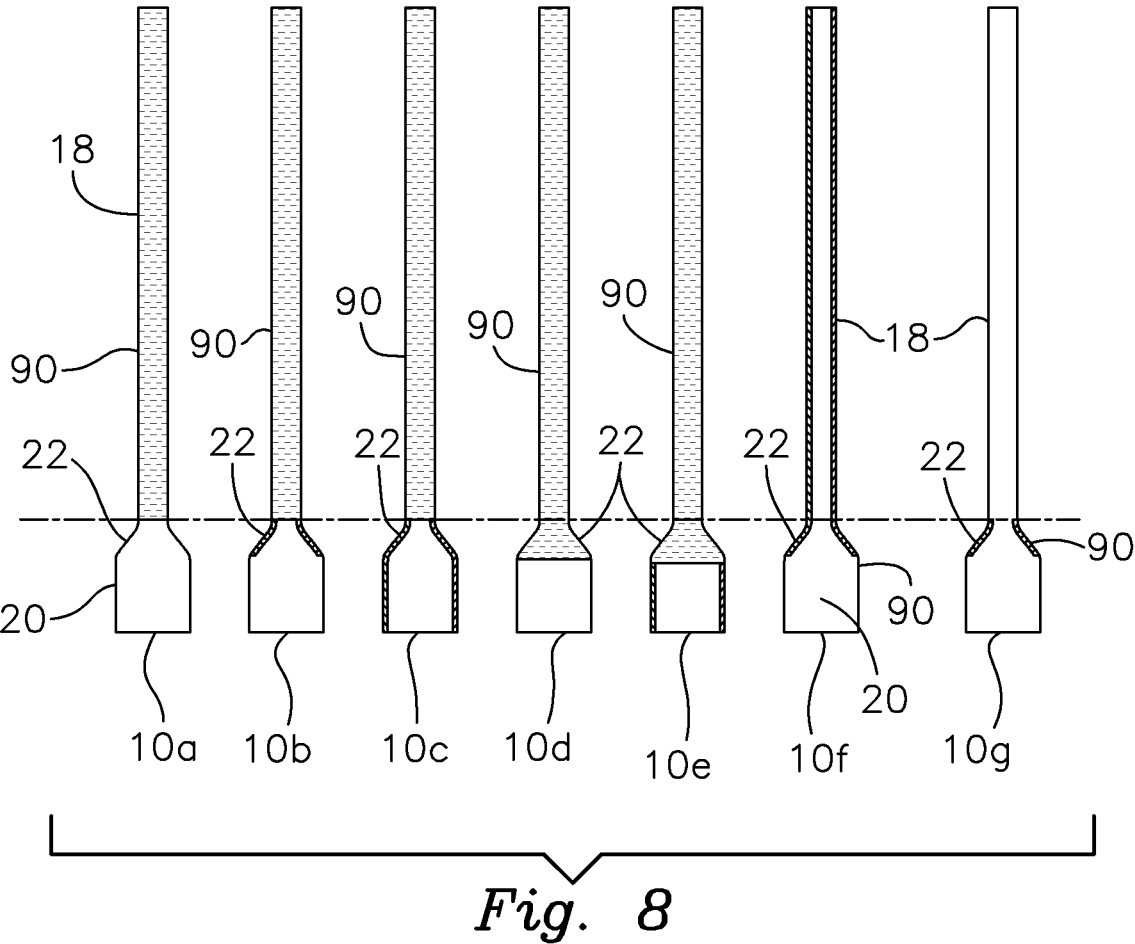
FIG. 8 is a plan view of a number of light carriers depicting opaque overmold sheathing applied to various selected respective sections of the intermediate, transition and channel sections of the light carrier in order to produce respective lighting effects for different types of surgery.

As shown in FIG. 8, the light carrier may be coated by an opaque overmold or analogous sheathing substance for restricting light projection from the carrier and thereby achieving different types of lighting effects. For example, in light carriers 25*a-e*, the intermediate section 18 of the carrier is coated by overmold 90. In carriers 10*d* and *e* the entire transition section is coated, whereas in 10*b* and *c* only the edges of the transition section are covered by an opaque material. In carriers 10*c* and *e*, the edges of the channel section are covered by an overmold. In light carriers 10*f* and *g* the intermediate section is fully exposed. Carrier 10*f* carries overmold on the edges of both its transition and channel sections whereas carrier 10*g* carries overmold only along the edges of its transition section. Each of these respective examples achieves a different illumination effect within the surgical tube. Alternative overmold configurations may be employed within the scope of this invention.

Figure 9:
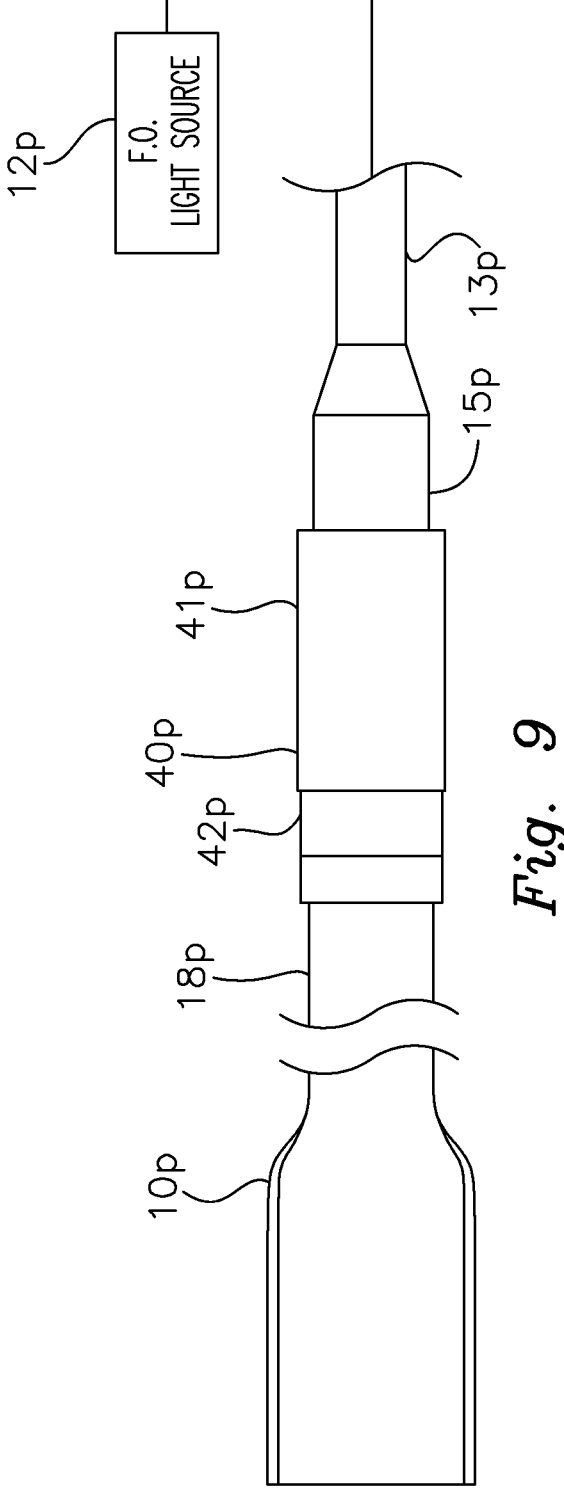
FIG. 9 is a top view of a preferred assembly for operably interconnecting the light carrier to a fiberoptic cable light source.
Figure 10:
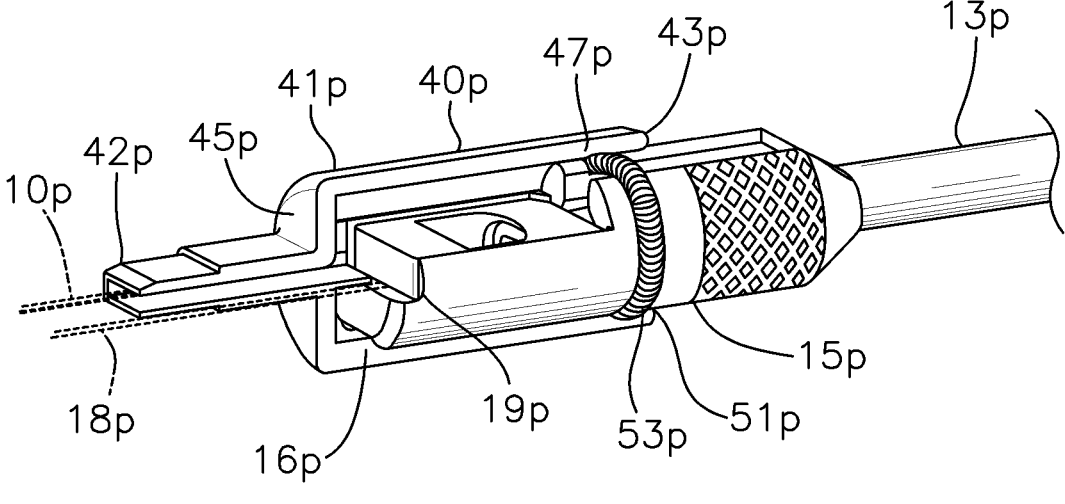
FIG. 10 is a partly cross sectional perspective view of the light carrier/fiberoptic cable connection shown in FIG. 9.

FIGS. 9-10 illustrate a preferred manner for interconnecting light carrier 10*p* to a fiberoptic light source 12*p*. In particular, light carrier 10*p* is constructed analogously to the previously described light carrier 10 but is shown as including a somewhat longer intermediate section 18*p*. Otherwise, it should be understood that the light carrier is constructed identically or substantially similarly to the previously described version. Fiberoptic light source 12*p* delivers light through a fiberoptic cable 13*p* to a flared or widened discharge end 15*p* of the cable.

Interface 40*p* operably interconnects light carrier 10*p* to fiberoptic cable 13*p* as follows. The interface comprises a tubular coupler 41*p* having an open leading end 43*p* and an opposite trailing end 45*p* from which extends a flat integral tubular connector 42*p*. The tubular coupler further includes an interior circumferential groove 47*p*. The connector includes a flat slot that extends through the connector and communicates with the interior of coupler 41*p*. The interior slot of flat tubular connector 42*p* receives the flat intermediate section 18*p* of light carrier 10*p* such that the inlet end 16*p* of light carrier 10*p* is received within the interior chamber of coupler 41*p*.

Figure 11:
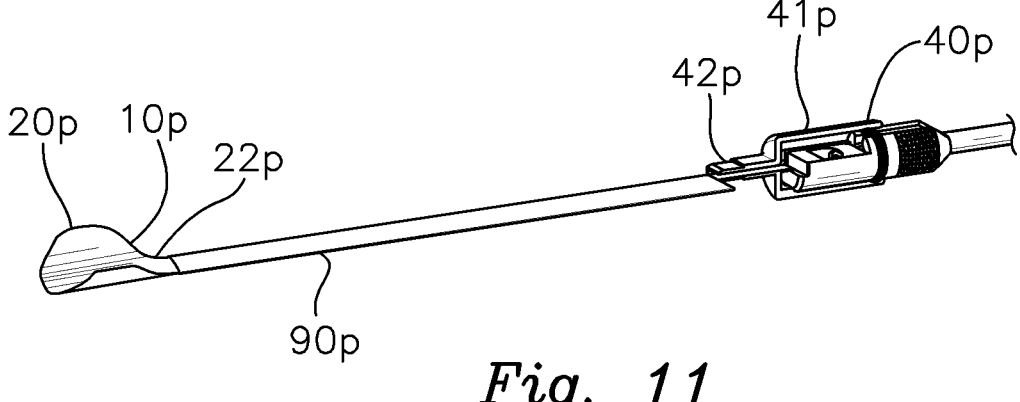
FIG. 11 is a partly cut away perspective view of the assembled light carrier and fiberoptic cable with the intermediate section of the light carrier covered by a light attenuating sheath.

The enlarged distal end 15*p* of cable 13*p* includes a terminal outlet 19*p* for discharging light from the fiberoptic light source 12*p*. The enlarged distal end 15*p* of the fiberoptic cable also includes a circumferential outer groove 51*p* that accommodates a coil garter spring 53*p*. Light carrier 10*p* is operably engaged with fiberoptic cable 13*p* by inserting enlarged light discharge end 15*p* of cable 13*p* into the interior chamber of tubular coupler 41*p* through open end 43*p*. The discharge end of the fiberoptic cable slides through the coupler 41 until spring 53*p* engages and seats in interior circumferential groove 47*p* of coupler 41*p*. The interface and fiberoptic cable are constructed such that the light inlet end 16*p* of light carrier 10*p* abuts the light discharge outlet 19*p* of cable 13*p*. The interface and light carrier thereby remain securely fastened to cable 13*p* due to the tight interengagement between coil spring 53*p* and the interior slot 47*p* of coupler 41*p*. As shown in FIG. 11, a light attenuating sheath or overmold 90*p* may be optionally formed over the entire intermediate section 18*p* of light carrier 10*p* such that the projection of potentially distracting light is eliminated along most of the light carrier's length. Light is projected only from channel 20*p* and transitional section 22*p*. As a result, enhanced beneficial illumination is focused directly upon the surgical site.

Figure 12:
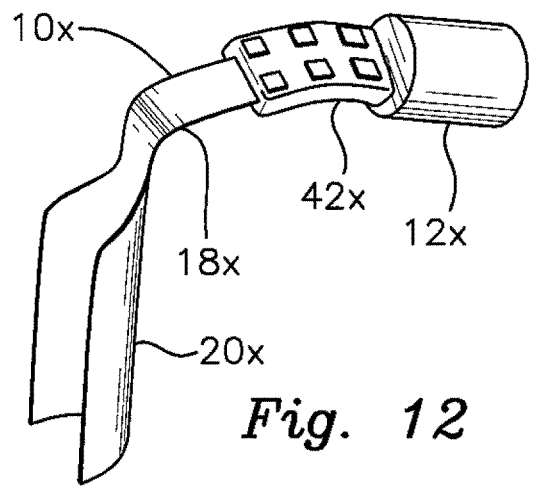
FIG. 12 is a perspective view of an alternative light carrier employing a longitudinally curved intermediate section and operably interconnected to a battery powered LED light source.
Figure 13:
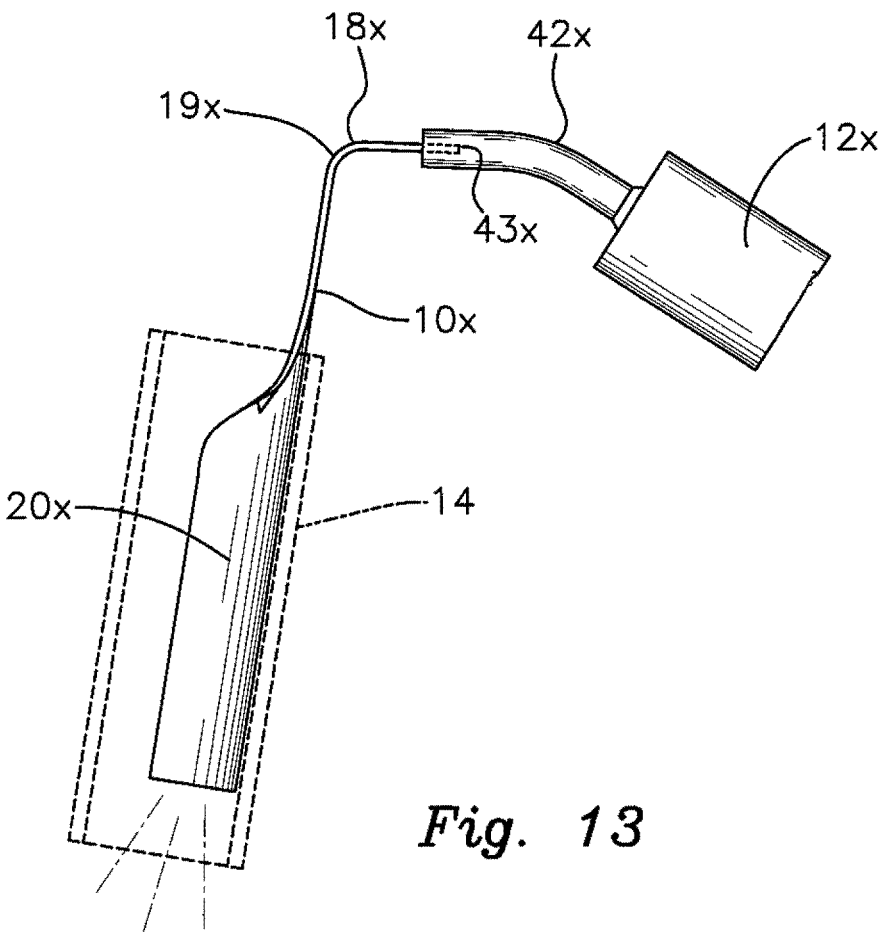
FIG. 13 is an elevational side view of the alternative light carrier of FIG. 12 operably inserted into a surgical tube in accordance with this invention to illuminate a surgical procedure.

An alternative battery-operated light carrier 10*x* is depicted in FIGS. 12 and 13. The light carrier 10*x* is constructed similarly to the previously described version and again includes a unitary or single-piece light conducting and projecting material for illuminating the interior of a surgical tube 14. Light carrier 10*x* is communicably connected to a portable battery powered LED light source 12*x* by means of a flat to round tubular light connector 42*x*. A preferred light source 12*x* is disclosed in U.S. Pat. No. 10,401,001, the details of which are incorporated by reference herein. The light connector includes an interior channel 43*x* that is communicably attached at a first end of channel 43*x* to a round light outlet port of light source 12x. An opposite flat end of channel 43x receives an intermediate section 18x of light carrier 10x and is communicably interengaged by a light inlet at the tip of section 18x. Unlike the previously described version, light carrier 10x employs an intermediate section 18x that includes an elbow 19x. This enables the light source 12x and connector 42x to be mounted to the surgical table at alternative orientations that permit more convenient placement of the channel section 20x into the tube 14. The intermediate section may be curved or angled at various other radii or degrees to achieve proper positioning and placement of the light carrier within the tube. As previously indicated, the curvature, size, shape, length and radius of the channel section may also be varied within the scope of this invention. The assembled carrier 10x and light source are disposable and especially suited for sterile, single use applications where the greater intensity lighting provided by a fiberoptic light source is not required.

Accordingly, this invention relates to a light carrier that is particularly effective for use with a surgical tube, as well as to the combination of a surgical tube and a light carrier that provides significantly improved and versatile illumination for medical and surgical procedures performed through the tube. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof. Although specific features of the invention are shown in some of the drawings and not others, this is for convenience only, as each feature may be combined with any and all of the other features in accordance with this invention.

What is claimed is:

1. An illuminated surgical tube assembly for use in a surgical or medical procedure, said assembly comprising:

a surgical tube having open upper and lower ends and an interior passageway that interconnects said open upper and lower ends, said interior passageway having an interior diameter; and a light conducting and projecting light carrier, said light carrier including an inlet section composed of a light conducting material for communicably interconnecting to a source of light, an intermediate section unitarily and communicably interconnected to said inlet section and composed of said light conducting material for transmitting light from said inlet section therethrough, and a laterally resilient and compressible channel section unitarily and communicably interconnected to said intermediate section, said channel section being composed of said light conducting material and including a light projecting outer surface portion; said channel section having a lateral width that is greater than said interior diameter of said interior passageway of said tube; said channel section for being laterally and resiliently compressed and inserted into said interior passageway of said surgical tube wherein said channel section is urged diametrically outwardly by a spring bias of said channel section to engage an interior wall of said interior passageway such that said light carrier is held at a selected longitudinal position within said surgical tube and light is conducted through and projected from said channel section and transmitted through said surgical tube to illuminate the procedure being performed.

2. The assembly of claim 1 in which said intermediate section includes a flat elongate strip.

3. The assembly of claim 1 in which said intermediate section includes an elongate strip that is longitudinally curved.

4. The assembly of claim 1 further including a light conducting transition section for unitarily and communicably interconnecting said intermediate section and said channel section, said transition section being configured such that said channel section is laterally wider than said intermediate section.

5. The assembly of claim 1 further including an opaque outer surface portion for restricting light projection therefrom.

6. The assembly of claim 5 in which said opaque outer surface portion is defined by an overmold that covers a portion of one or more of said channel and said intermediate sections to restrict light projection therefrom.

7. The assembly of claim 6 in which said overmold covers at least a portion of said transition section for restricting the projection of light therefrom.

8. The assembly of claim 1 in which said channel section is resiliently biased to laterally conform to said interior wall of said interior passageway into which said channel section is inserted.

9. The assembly of claim 1 in which said channel section is maintained at said selection position within said tube exclusively by said lateral spring bias of said channel section.

10. An illumination system for engaging a surgical tube and directing light from a light source through the surgical tube to illuminate a medical procedure being performed through the surgical tube, said system comprising:

a light carrier including a light inlet section composed of a light conducting material, an intermediate section unitarily and communicably connected to said inlet section and composed of said light conducting material for transmitting light from said inlet section therethrough, and a laterally concave channel section unitarily and communicably interconnected to and extending distally from said intermediate section, said channel section being composed of said light conducting material and including a light projecting outer surface portion; and an interface for communicably interconnecting said light inlet section to a source of light, which said interface includes a tubular coupler having a flat slot that receives said inlet section and an opening for receiving a light discharge outlet of a fiberoptic cable communicably connected to the light source; said fiberoptic cable carrying an annular spring that interengages a circumferential interior groove in said tubular coupler to secure said light carrier to said cable with said inlet section of said light carrier abutting said light discharge outlet of said cable said channel section being insertable into the surgical tube such that light from said light source is transmitted through said interface and said light carrier, projected from said channel section and directed through the surgical tube to illuminate the surgical procedure being performed.

11. The assembly of claim 10 in which said channel section is laterally wider than said intermediate section.

12. An illuminated surgical tube assembly for use in a surgical or medical procedure, said assembly comprising:

a surgical tube having open upper and lower ends and an interior passageway that interconnects said open upper and lower ends, said interior passageway having an interior diameter;

a light carrier including a flat light inlet section composed of a light conducting material, a flat intermediate section unitarily and communicably connected to said inlet section and composed of said light conducting material for transmitting light from said inlet section therethrough, and a laterally resilient and compressible channel section unitarily and communicably interconnected to and extending distally from said intermediate section, said channel section being composed of said light conducting material and including a light projecting outer surface portion; said channel section having a lateral width that is greater than said interior diameter of said interior passageway of said tube; and an interface that communicably interconnects said light inlet section to a source of light, which said interface includes a round to flat tubular coupler having a round opening for receiving and communicably connecting to a round light discharge outlet of said source of light and a flat slot that communicates with said round opening for receiving and communicably connecting to said flat inlet section and at least a portion of said flat intermediate section of said light carrier;

said channel section being laterally compressed and inserted into said surgical tube wherein said wherein said channel section is urged diametrically outwardly by a spring bias of said channel section to engage an interior wall of said interior passageway such that said light carrier is held at a selected position within said surgical tube and such that light from said light source is transmitted through said interface and said light carrier, projected from said channel section and directed through the surgical tube to illuminate the surgical procedure being performed.

13. The assembly of claim 12 in which said source of light includes a battery powered LED light light source.

14. The assembly of claim 12 in which said source of light includes a fiberoptic light source communicably connected to said round opening of said interface.

15. The assembly of claim 12 in which said spring bias of said channel section urges said channel section into a flat condition when said channel section is not inserted into said interior passageway of said tube.

16. The assembly of claim 12 in which said channel section is maintained at said selection position within said tube exclusively by said lateral spring bias of said channel section.

* * * * *